(12) United States Patent
Matsumoto (10) Patent No.: US 8,246,578 B2
(45) Date of Patent: Aug. 21, 2012

(54) PUNCTURE DEVICE

(75) Inventor: Atsushi Matsumoto, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/934,750

(22) PCT Filed: Dec. 22, 2008

(86) PCT No.: PCT/JP2008/073311
§ 371 (c)(1),
(2), (4) Date: Sep. 27, 2010

(87) PCT Pub. No.: WO2009/118967
PCT Pub. Date: Oct. 1, 2009

(65) Prior Publication Data
US 2011/0015659 A1    Jan. 20, 2011

(30) Foreign Application Priority Data
Mar. 28, 2008 (JP) .................. 2008-087202

(51) Int. Cl.
*A61M 5/00* (2006.01)
(52) U.S. Cl. .................. 604/115; 604/116; 606/185
(58) Field of Classification Search .................. 24/563; 128/226; 604/115, 116, 164.04, 174–180, 604/351; 606/167, 185, 201, 203, 204
See application file for complete search history.

(56) References Cited

U.S. PATENT DOCUMENTS

| 3,814,080 A | 6/1974 | Norman | |
|---|---|---|---|
| 4,314,568 A | 2/1982 | Loving | |
| 5,254,095 A * | 10/1993 | Harvey | 604/115 |
| 2003/0171716 A1 | 9/2003 | Ejlersen | |
| 2007/0156096 A1 * | 7/2007 | Sonoda et al. | 604/174 |
| 2008/0015624 A1 * | 1/2008 | Sonoda et al. | 606/185 |
| 2008/0167620 A1 * | 7/2008 | Adams et al. | 604/180 |
| 2010/0069848 A1 * | 3/2010 | Alferness et al. | 604/151 |

FOREIGN PATENT DOCUMENTS

| JP | 2005-518253 A | 6/2005 |
|---|---|---|
| JP | 2007-117616 A | 5/2007 |

OTHER PUBLICATIONS

International Search Report (PCT/ISA/210) issued on Mar. 24, 2009, by Japanese Patent Office as the International Searching Authority for International Application No. PCT/JP2008/073311.

* cited by examiner

*Primary Examiner* — Nicholas D Lucchesi
*Assistant Examiner* — Gerald Landry, II
(74) *Attorney, Agent, or Firm* — Buchanan Ingersoll & Rooney PC (57) ABSTRACT

A puncture device includes a first base plate; a second base plate; a base plate connection part having flexibility and connecting the first base plate and the second base plate in a horizontal direction; an adhesive means provided to surfaces in a same direction of the first base plate and the second base plate; and a puncture needle moving means provided in the first base plate and movably supporting a puncture needle. The puncture needle is supported away from a surface of the adhesive means a given distance and movable substantially in parallel to the surface of the adhesive means.

16 Claims, 11 Drawing Sheets

PUNCTURE DEVICE

TECHNICAL FIELD

The present invention relates to a puncture device which punctures skin from the surface of the skin and places a needle tip in a predetermined region (for example, dermis) of the skin.

BACKGROUND ART

In dermis, density of capillary blood vessels is higher as compared with epidermis and subcutaneous tissue, and terminals of lymph vessels are present, so that it is known that particularly a directly injected drug moves to blood vessels or lymph vessels relatively fast, and the absorption rate to absorb the drug in body fluids becomes faster. Especially, in dermis, it is possible to cause drugs using macromolecular material, such as hormone, antibody medicine, cytokine, etc., to be efficiently absorbed in blood. Further, it is known that dermis is a place of relatively effective immunity, and it is possible to save a dosage of vaccine and to increase sensitization of vaccine.

Also, it is known that in a grown-up man, dermis is present at a given depth from the body surface (surface of a stratum corneum). This means in other words that when injecting a drug into dermis, it is possible to use puncture needles of the same length (depth) to adults.

Generally, the thickness of dermis is about 1 mm-4 mm (average value is 1 mm-2 mm) with reference to a vertical direction relative to the body surface. Further, in general skin structure, dermis is present in the skin, being sandwiched between epidermis with the thickness of about 0.06 mm-0.1 mm including a stratum corneum, and subcutaneous tissue. Accordingly, it is difficult to correctly insert a drug solution supplying opening of a puncture device, for example, a needle tip of a puncture needle, into dermis that is present between epidermis and subcutaneous tissue, and if the needle tip is accidentally inserted in subcutaneous tissue, etc., a problem is caused that a drug cannot be efficiently absorbed.

Recently, it is tried to administer medicine using the above-described macromolecular material to dermis as a target, in a sustained manner or as one-shot administration, however, in such a case, the above-described problem becomes conspicuous.

Background puncture devices of this kind include, for example, the one described in Patent Document 1. Patent Document 1 describes a puncture device for which the present applicant previously filed a patent application. The puncture device according to Patent Document 1 (hereinafter called as "first background example") is a puncture device puncturing skin with a puncture needle. The puncture device includes a puncture needle moving means movably holding a puncture needle, a fixing unit having a flat plane to be fixed to the body surface and in which the puncture needle moving means has been provided, and a hinge provided to the fixing unit and configured to raise the skin upward relative to the body surface by rotating, and is configured such that the puncture needle is moved along the flat plane of the fixing unit to puncture the skin raised by the hinge.

Other examples of background puncture devices include the one described in Patent Document 2. Patent Document 2 describes an injection device and an injection method. The injection device according to Patent Document 2 (hereinafter referred to as "second background example") is an injection device for giving an injection to skin at a given depth, including a skin positioning means for carrying out positioning relative to a part in a region of skin such that at least a portion of the part of the skin can be held raised above or dented below the region of the skin, an injection needle, and a means for guiding the injection needle to slide beneath the skin positioning means to an injection position where an end of the needle lies at a given distance below the skin positioning means.

Patent Document 1: Japanese Patent Laid-Open No. 2007-117616
Patent Document 2: Japanese Patent Laid-open No. 2005-518253

DISCLOSURE OF THE INVENTION

Problems to be Solved by the Invention

However, in the case of the first background art, after placing an adhesive pad in a predetermined position of the body surface, by holding a rotation piece of a hinge and rotating it upward, the skin adhered to an adhesive film provided to the rotation piece of the hinge is raised upward and thereby dermis is raised so as to be parallel to the rotation piece of the hinge. In this condition, after a placement member fixedly supporting an injection device is slid in a tip direction and a tip of the puncture needle is brought close to a puncture region, the puncture needle is caused to puncture dermis by operation of a plunger. And, it is necessary that the operator manually adjusts and sets the rotation angle of the rotation piece at a predetermined angle so that the rotation angle of the rotation piece becomes substantially parallel to the moving direction of the puncture needle. Therefore, there has been a problem that proficiency is required for setting the rotation angle of the rotation piece, and angle adjustment of the rotation piece for aligning the drug solution outlet of the puncture needle with dermis is difficult for beginners.

Also, in the case of the second background art, after removing a release tape and putting the adhesive undersurface to skin, the user pushes a manually-fit type slider along the upper surface of an upper part, and thereby a cam plate moves to the front along runners from an initial position to a final position. Then, the base plate of a bell crank and a small area of the skin to which the base plate of the bell crank has been attached are rotated around a pivot to be relatively inclined relative to the undersurface of a lower part at the angle of about 20 degrees. Thereby, the needle extends under the small area of the skin at a predetermined depth in parallel to the skin surface, and it becomes possible to push out an object substance for injection from the needle to be put in the skin. In this case, because the puncture needle is inserted obliquely relative to dermis, the depth (insertion depth) of the puncture needle within the dermis becomes short, so that there has been a problem that proficiency is required for aligning the drug solution outlet of the needle tip with dermis and alignment relative to dermis is difficult for beginners.

Also, the first background art and the second background art pick up or push down skin obliquely, and the density of obliquely deformed skin becomes nonuniform. Therefore, even if the puncture needle is caused to puncture a given distance from an adherend surface, depending on the distance the puncture needle enters skin, the needle tip does not necessarily lie at a given depth of the skin.

The problem to be solved is that in puncture devices of background art as described above, proficiency is required for aligning the drug solution outlet provided in the needle tip of a puncture needle with dermis, and it is difficult for beginners to align the needle tip (drug solution outlet) with dermis.

Means for Solving the Problems

The present invention is constituted by including a first base plate, a second base plate, an adhesive means provided to surfaces in the same direction of the first base plate and the second base plate, and a puncture needle moving means provided to the first base plate and movably supporting a puncture needle. The main feature of the present invention is in that the puncture needle is supported away from the surface of the adhesive means a predetermined distance and movably substantially in parallel to the surface of the adhesive means, and when the skin to which the adhesive means had adhered has been picked up by being pinched by the first base plate and the second base plate, the puncture needle is moved by the puncture needle moving means to puncture the picked up skin.

The present invention is characterized in that the puncture needle moving means includes a slide member supporting the puncture needle, and a guide member supporting the slide member in a linearly-movable manner.

Further, the present invention is characterized in that the puncture needle moving means includes a locking means capable of locking the slide member at a given position of the guide member and releasing such locking.

And, the present invention is characterized in that the guide member is constituted by a cylindrical body having a penetration hole opened at both ends thereof, and a guide part preventing rotation and enabling only linear movement of the slide member is provided in the penetration hole.

Further, the present invention is characterized in that the first base plate, the second base plate, and the base plate connection part are integrally formed by synthetic resin.

The present invention is characterized in that in the puncture needle, a blade edge is formed at a tip, and the slide member supports the puncture needle with an inclined surface of the blade edge directed in a direction substantially vertical to the surface of the adhesive means.

Also, the present invention is characterized in that one end of a drug solution injection port is connected to a base end of the puncture needle, within the slide member.

Effects of the Invention

According to the present invention, it is possible to set the plane direction of dermis parallel relative to the axial direction of the puncture needle, by picking up skin through two base plates, after causing the puncture device to adhere to the skin. From such a condition, by causing the puncture needle to puncture skin by operating the puncture needle moving means, it is possible to cause the needle tip (drug solution outlet) to surely reach a given region (for example, dermis) of the skin, and even a beginner can cause the needle tip (drug solution outlet) of the puncture needle to coincide with dermis simply and reliably.

EXPLANATION OF SYMBOLS

1: puncture device
2, 18: fixing unit
3: moving unit
4: first base plate
5: second base plate
6: guide member
6c: inclined surface part
7: adhesive tape (base plate support member)
8, 9: anti-slip part
11: release paper
12, 19: base plate connection part 14: guide part
15: engagement reception part
16: claw reception unit
21: slide member
22: puncture needle
23: connection tube
24: drug solution injection port
25: slide part
26: head part
27: ridge part
28: stepped part
30: drug solution outlet
35: lock lever
37: hinge part
38: lock claw
D: dermis
E: epidermis
S: subcutaneous soft tissue

BEST MODE FOR CARRYING OUT THE INVENTION

Below, description will be made referring to drawings, with respect to a best mode for carrying out a puncture device of the present invention. Note that the present invention is not limited to the following embodiment.

Figure 1:
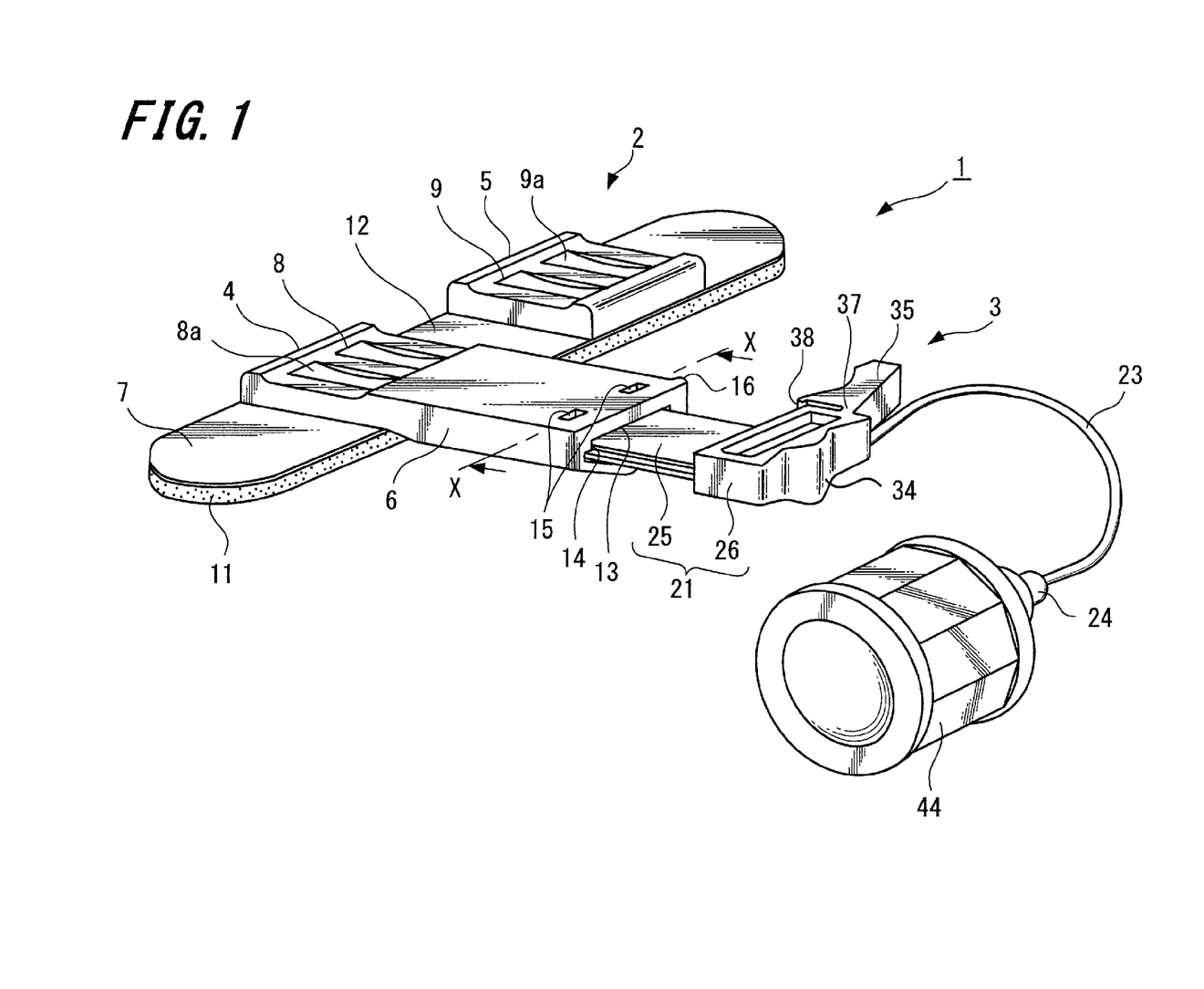
FIG. 1 is a perspective view illustrating a first embodiment of a puncture device of the present invention.
Figure 2:
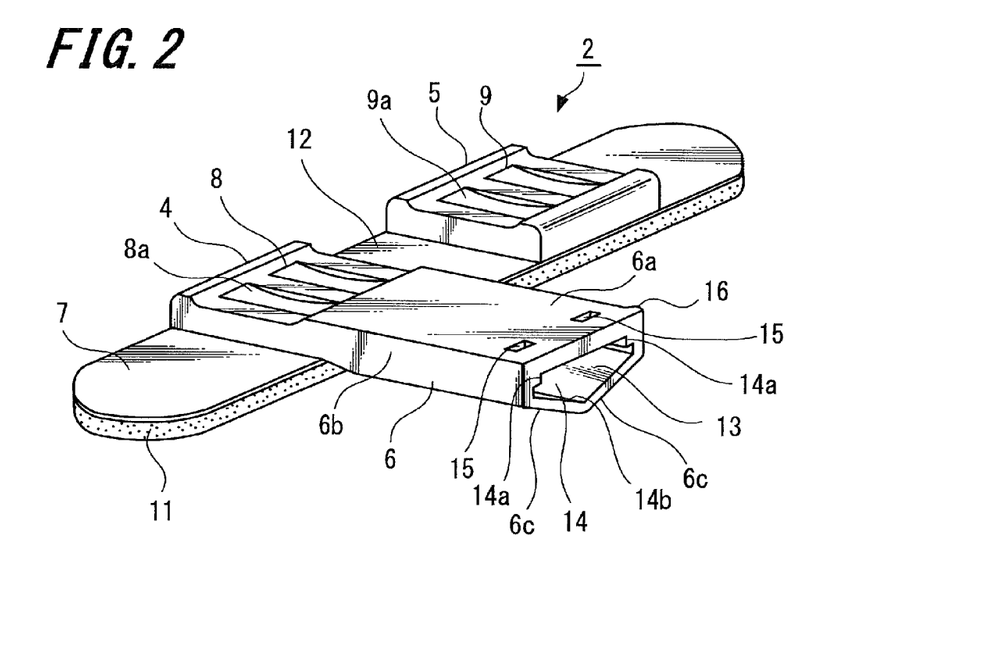
FIG. 2 is a perspective view illustrating a first example of a fixing unit of the puncture device of FIG. 1.
Figure 3:
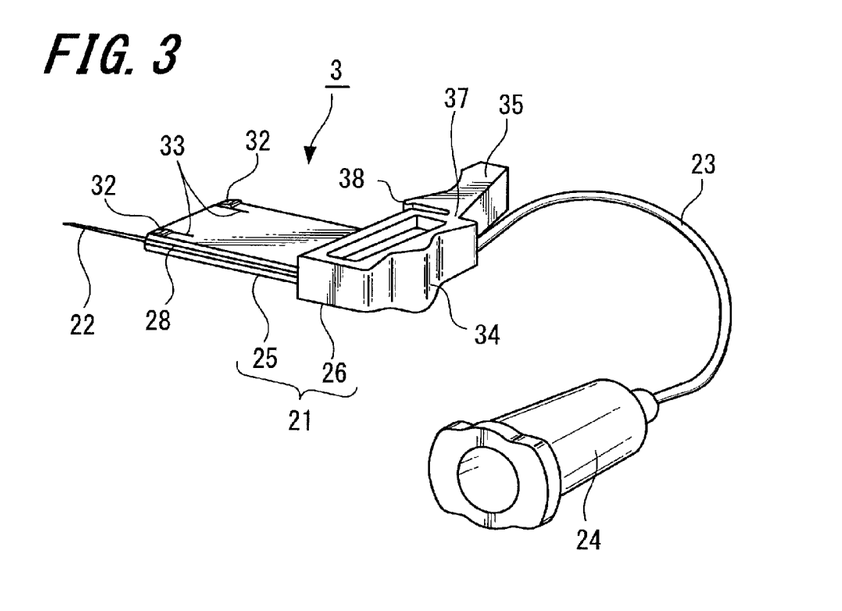
FIG. 3 is a perspective view of a moving unit of the puncture device illustrated in FIG. 1, when viewed from one surface side.
Figure 4:
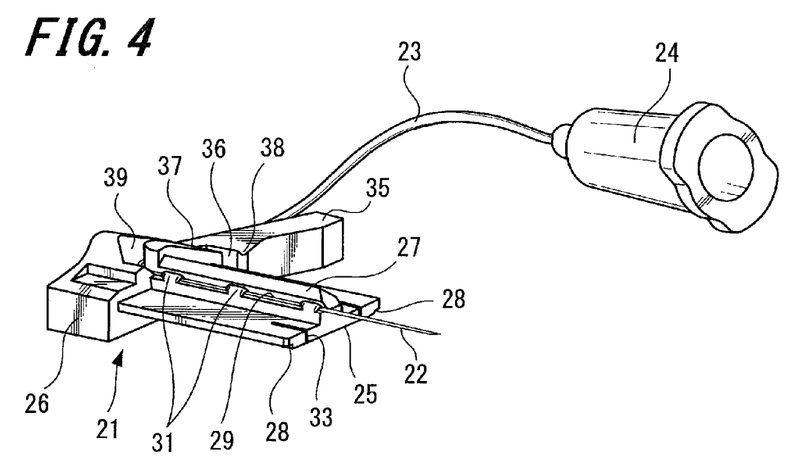
FIG. 4 is a perspective view of the moving unit of the puncture device illustrated in FIG. 1, when viewed from the other surface side.

FIG. 1 is a perspective view illustrating a first embodiment of a puncture device of the present invention in an assembled condition. FIG. 2, FIG. 3, and FIG. 4 are perspective views, respectively, illustrating the puncture device of FIG. 1 by splitting it.

As illustrated in FIG. 1 through FIG. 4, a puncture device 1 as the first embodiment of a puncture device of the present invention includes a fixing unit 2 for fixing the puncture device 1 to skin of the body, and a moving unit 3 configured to be held movable forward and backward relative to the fixing unit 2.

As illustrated in FIG. 2, the fixing unit 2 includes a first base plate 4, a second base plate 5, a guide member 6, which is formed integrally with the first base plate 4, and an adhesive tape 7, which is a concrete example of a base plate support member fixing and supporting the first base plate 4 and the second base plate 5. The first base plate 4 consists of a flat block-like member formed in a quadrangle having the size of about a thumb of man. On one surface of the first base plate 4 provided is an anti-slip part 8 which serves as a member preventing a thumb from slipping when the thumb is put on. The anti-slip part 8 is constituted in this example by two long grooves 8a which are parallel to each other, however, the anti-slip part 8 may include three pieces or more of the long groove 8a or only one piece of the long groove 8a. Further, other examples of the anti-slip part 8 may include a concave part in a circular, elliptical or other shape, and a convex part in an oblong, elliptical, arc, rectangular or other shape.

The second base plate 5 has substantially the same shape and size as those of the first base plate 4. That is, the second base plate 5 consists of a flat block-like member formed in a quadrangle having the size of about a thumb of man. On one surface of the second base plate 5 provided is an anti-slip part 9, which serves as a member preventing a forefinger (or middle finger) from slipping when the forefinger (or middle finger) is put on. The anti-slip part 9 is constituted by two long grooves 9a which are parallel to each other, like the first base plate 4, however, may include three pieces or more of the long groove 9a or only one piece of the long groove 9a. Further, other examples of the anti-slip part 9 may include a concave part in circular, elliptical or other shapes, or a convex part in oblong, elliptical, arc, rectangular, or other shapes.

The adhesive tape 7 is formed by a strip-like flexible member having substantially the same width as those of the first base plate 4 and the second base plate 5. The adhesive tape 7 is formed by coating an adhesive, such as rubber elastomer and acrylic resin, on a base material, such as cellophane, a polyvinyl chloride film, a woven cloth, etc. By using such a base material, sufficient flexibility is given to the adhesive tape 7, and thereby the adhesive tape 7 is constituted so as to easily bend along the skin. An adhesive is coated on the whole area of one surface of the adhesive tape 7, and a release paper 11 is detachably attached to the surface of the adhesive tape 7 where the adhesive is present. Note that a medical agent such as lidocaine, etc. can be contained in the adhesive. In this case, by causing lidocaine, etc. to be gradually released from the adhesive, it is possible to reduce injection pain when continuous administration is carried out using a pump.

The first base plate 4 and the second base plate 5 are fixed to a surface of the adhesive tape 7 opposite to the surface where the adhesive has been coated, with a predetermined interval between them in a longitudinal direction. Regarding the fixing means for fixing the first base plate 4 and the second base plate 5 to the adhesive tape 7, the first base plate 4 and the second base plate 5 may be attached using an adhesive or integrally joined by thermal fusion, and it is possible to apply other fixing means appropriately. The portion between the first base plate 4 and the second base plate 5 of the adhesive tape 7 constitutes a base plate connection part 12 connecting the first base plate 4 and the second base plate 5 in a flexible and deformable manner.

The guide member 6 is integrally formed continuing from one side of the first base plate 4. That is, the guide member 6 is provided continuing from one side of the first base plate 4 so as to protrude toward one side in the width direction perpendicular to the longitudinal direction of the adhesive tape 7. The guide member 6 consists of a cylindrical body in a pentagon shape in cross section, having a penetration hole 13 opened at both ends thereof. Thereby, the guide member 6 includes a flat surface part 6a continuing to a surface of the first base plate 4 where the anti-slip part 8 is provided, right-and-left side surface parts 6b, 6b continuing to both sides of the flat surface part 6a and formed as substantially perpendicular planes, and right-and-left inclined surface parts 6c, 6c formed as a convex part in a chevron shape continuing from the right-and-left side surface parts 6b, 6b.

The inclined surface parts 6c, 6c side of the guide member 6 protrudes widely outward from the surface of the first base plate 4 where the adhesive tape 7 is fixed (hereinafter referred to as a reference plane). By the inclined surface parts 6c, 6c forming a protrusion part of the guide member 6, when the skin has been picked up as described later, a step is provided in a puncture position of the skin, and it comes to that the needle tip is on the same level as dermis.

The penetration hole 13 provided in the guide member 6 having such an exterior shape is formed as a hole in an arrow shape, being convex on the side of the right-and-left inclined surface parts 6c, 6c. By two guide parts 14a, 14a of the penetration hole 13, provided at both corners of the flat surface part 6a, and an obtuse angle part 14b formed on the tip end side of the arrow shape, a guide part 14 is constituted, which movably supports a slide member described later while preventing rotation and allowing only linear movement thereof. Both of the guide parts 14a, 14a are formed so as to continue from one end to the other end of the penetration hole 13.

Also, on the side of the flat surface part 6a of the guide member 6 opposite to the side where the first base plate 4 is provided, an engagement reception part 15 is provided, which prevents the slide member from falling off. The engagement reception part 15 is formed as a quadrangular hole penetrating through front and back surfaces of the flat surface part 6a, however, it may be formed as a penetration hole in a circular or elliptical shape, and further, it may be a concave part with a bottom part, which is opened only in the internal surface of the penetration hole 13. Further, a claw reception part 16, which also prevents the slide member from falling off, is provided to one side surface part 6b of the guide member 6.

As the material of the first base plate 4, the guide member 6, and the second base plate 5, for example, PP (polypropylene), PC (polycarbonate), and other hard plastics can be used. Note that it is desirable that the guide member 6 is formed by transparent material to secure internal visibility. Also, it is sufficient if the guide member 6 is the one having such a shape that the slide member can be movably supported, and for example, it may be a cylindrical body in a circular shape, an elliptical shape, etc.

Figure 5:
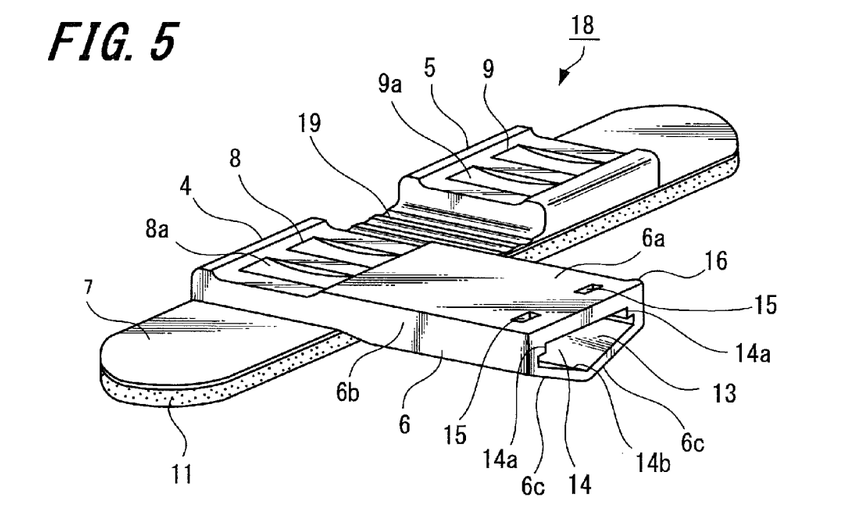
FIG. 5 is a perspective view of a second example of the fixing unit of the puncture device of FIG. 1.

FIG. 5 illustrates an exemplary variation of the fixing unit 2 illustrated in FIG. 2. A fixing unit 18 in this example is the one formed by forming the base plate connection part 12 in the fixing unit 2 integrally with the first base plate 4 and the second base plate 5 with the same material. The other portions of the fixing unit 18 are substantially the same as the fixing unit 2, so that description will be made only with respect to portions that are different from the fixing unit 2, and overlapped explanation will be omitted with the same portions denoted with the same reference symbols.

The point of a base plate connection part 19 of the fixing unit 18 that is different from the base plate connection part 12 is that the first base plate 4 and the second base plate 5 are integrally molded, for example, by injection molding, etc. As described later with reference to usage examples, when in use, the base plate connection part 19 needs to have sufficient flexibility so that it can easily bend when the user has picked up the first base plate 4 and the second base plate 4 with finger tips. Therefore, in this example, the base plate connection part 19 is formed sufficiently thin as compared with the first base plate 4, etc. Further, in the base plate connection part 19, long grooves continuing in the width direction are formed at a plurality of places in the longitudinal direction, and thereby bending deformation is facilitated.

As illustrated in FIG. 3 and FIG. 4, the moving unit 3 includes a slide member 21 movably supported by the guide member 6, and a puncture needle 22 fixed to the slide member 21. The slide member 21 is connected to a drug solution injection port 24 through a connection tube 23.

Figure 6:
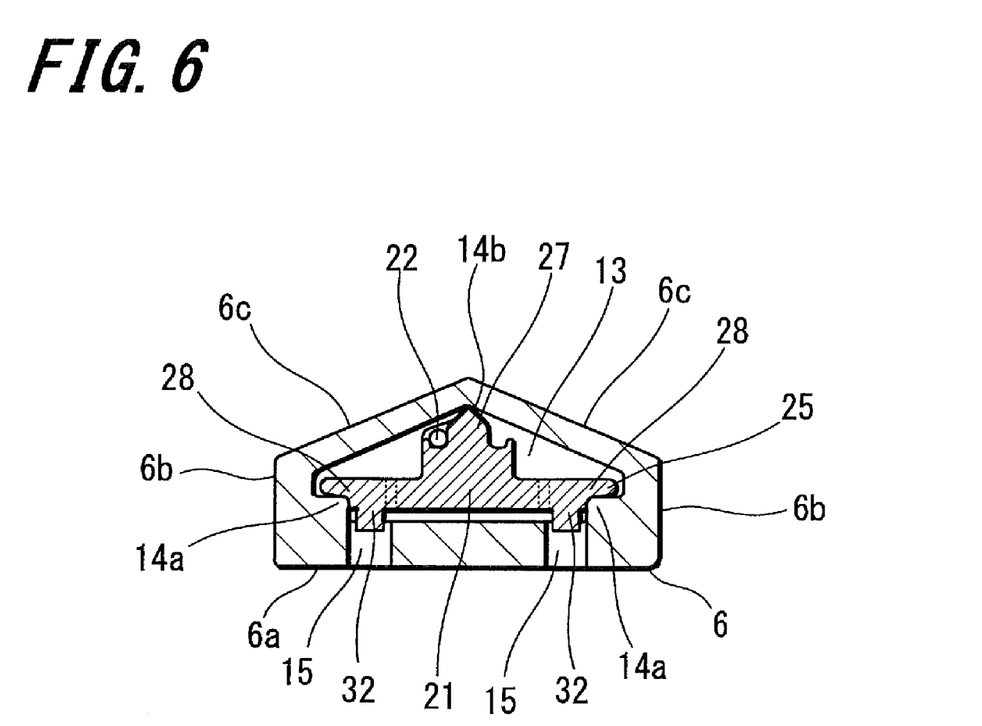
FIG. 6 is a cross section at an X-X line portion of the puncture device illustrated in FIG. 1.

The slide member 21 includes a slide part 25, which is slidably fit into the penetration hole 13 of the guide member 6, and a head part 26, which is continuously formed at one end of the slide part 25. The slide part 25 consists of a tabular part thinly formed so that it can be inserted in the penetration hole 13, and a ridge part 27 continuing in the longitudinal direction is provided substantially at the center of one surface of the slide part 25. Thereby, as illustrated in FIG. 6 in cross section, the cross section shape in the direction perpendicular to the longitudinal direction of the slide part 25 is in a substantially T-like shape.

Also, at both edges of the surface of the slide part 25 on the opposite side of the ridge part 27, stepped parts 28 chamfered substantially at 90 degrees are provided, respectively. The stepped parts 28, 28 are slidably engaged with the guiding parts 14a, 14a that are provided in the penetration hole 13 of the guide member 6. The top of the ridge part 27 is formed in a ridge shape forming a triangle in cross section. The top of the ridge part 27 is slidably engaged with the internal surface of the obtuse part 14b provided in the penetration hole 13. By the function of the guide part 14 constituted by the guiding parts 14a, 14a and the obtuse part 14b, the slide member 21 is movably supported while being prohibited from rotating and enabled only to move linearly, relative to the guide member 6.

Figure 7:
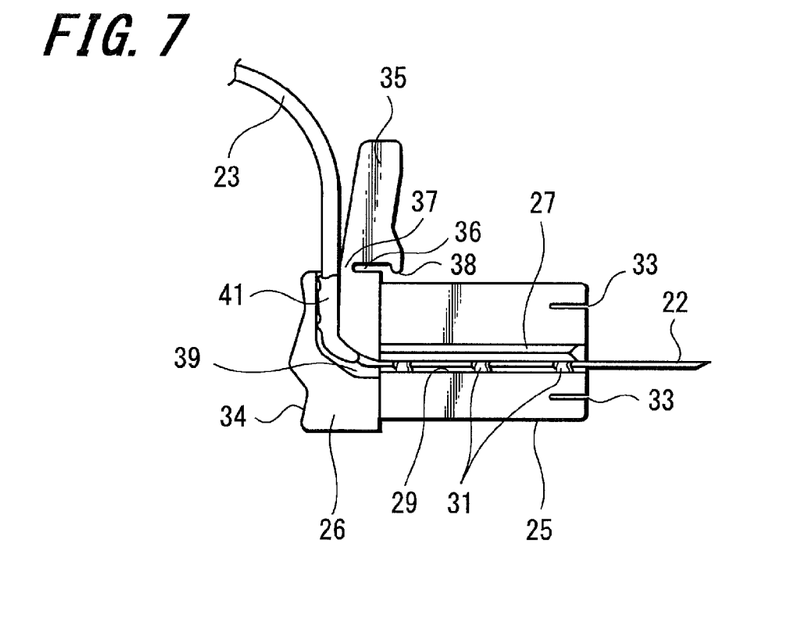
FIG. 7 is a plan view of the moving unit of the puncture device illustrated in FIG. 1, viewed from one surface side.
Figure 8:
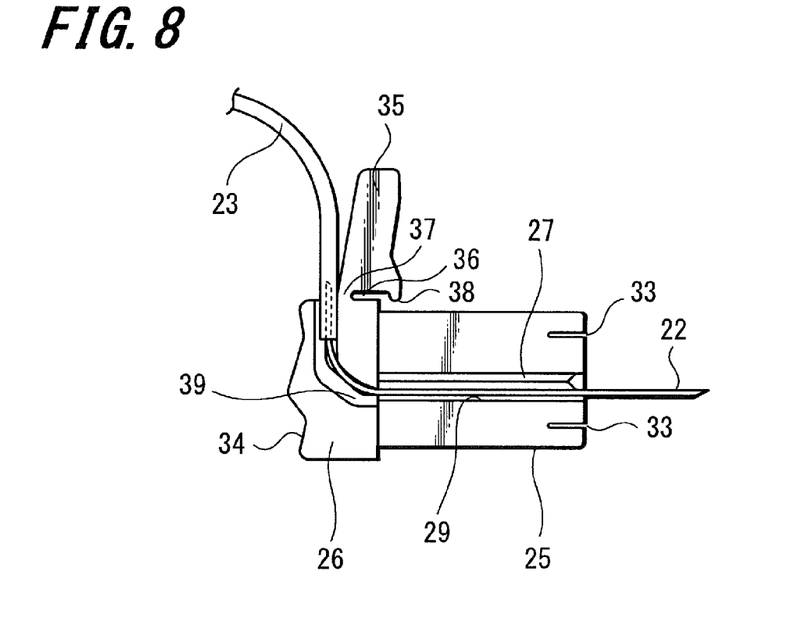
FIG. 8 is a plan view of the moving unit illustrated in FIG. 7, in which a needle holding part holding a puncture needle and a fixing member have been removed.

On one side of the ridge part 27 of the slide part 25, a puncture needle storage part 29 which supports the puncture needle 22 is provided. As illustrated in FIG. 7 and FIG. 8, the puncture needle storage part 29 is formed as a long groove continuing along the ridge part 27. The outer diameter of the puncture needle 22 stored in the puncture needle storage part 29 is about 0.05 mm-2.0 mm, although it may slightly change depending on usage, etc. of the puncture device 1, and specifically, it is preferable that the outer diameter is about 0.1 mm-0.4 mm. In addition, the puncture needle 2 may be a conically-shaped cylindrical body in which the shaft diameter has been thinned on the tip side, and also, it may be a cylindrical body in which the shaft diameter has been made equal. In the puncture needle storage part 29, a needle holding part 31 for preventing falling off of the puncture needle 22 is provided at a plurality of places. FIG. 7 illustrates a state that the puncture needle 22 is held by the needle holding part 31, and FIG. 8 illustrates a state that the needle holding part 31 has been removed.

As the material of the puncture needle 22, for example, metal materials are given, such as stainless steel, aluminum, aluminum alloy, titanium, titanium alloy, etc. The puncture needle 22 is made, for example, by roundly bending a flat plate so as to be formed in a cylindrical shape, and thereafter, by joining connection portions thereof by laser processing, etc. At the tip of the puncture needle 22, a blade edge is formed as an inclined part inclined at an appropriate angle (for example, about 30 degrees), and an elliptical drug solution outlet 30 is opened in the inclined part.

Further, in the tip part of the surface of the slide part 25 on the side opposite to the side where the ridge part 27 is present, an engagement convex part 32 for preventing falling off of the slide member 21 from the guide member 6 and positioning the slide member 21 in a predetermined position is provided at two places. Two engagement convex parts 32 are arranged on both ends in the width direction of the slide part 25. To give suitable elasticity to these engagement convex parts 32, slits 33 extending in the longitudinal direction are provided at the tip of the slide part 25. These two convex engagement parts 32 are detachably engaged with the two engagement reception parts 15 of the guide member 6.

As illustrated in FIG. 3 and FIG. 4, the head part 26 of the slide member 21 consists of a block-like part, which is, as compared with the slide part 25, smaller in size in the longitudinal direction, however, larger in size in the width direction and the depth direction, and is formed integrally with the slide part 25. A concave-convex part 34, which serves as an anti-slip when performing a pressing operation, is provided in the surface of the head part 26 opposite to the side where the slide part 25 is present. Further, a lock lever 35 protruding sideways is integrally provided in one side surface of the head part 26.

In the lock lever 35, a hinge part 37 is formed by providing a cutout 36 in the base part. Thereby, the lock lever 35 is rotatable in the horizontal direction around the hinge part 37. At the tip part of the cutout 36 of the lock lever 35, a lock claw 38 is provided, which is attachable and detachable relative to the claw reception part 16 provided in the guide member 6. The lock claw 38 is configured to be engaged with the claw reception part 16 in a free state in assembling so as to be held in a locked state. And, it is configured such that the locked state of the lock claw 38 relative to the lock reception part 16 is released by rotating the lock claw 38 toward outside resisting the resistance force to the rotation of the lock lever 35 at the hinge part 37.

Further, as illustrated in FIG. 7 and FIG. 8, in the head part 26 of the slide member 21, a hold groove 39 for holding a joining part joining the base of the puncture needle 22 and one end of the connection tube 23 is provided. One end of the hold groove 39 is opened at the front surface of the head part 26, the hold groove 39 turns around 90 degrees in a midway part, and the other end of the hold groove 39 is opened at the side surface of the head part 26 at the back of the lock lever 35. Therefore, the base of the puncture needle 22 is formed to bend 90 degrees, and protrudes sideways. The joining part of the puncture needle 22 and the connection tube 23 is fixed in the hold groove 39 by a fixing member 41 such as an adhesive, etc.

Figure 15:
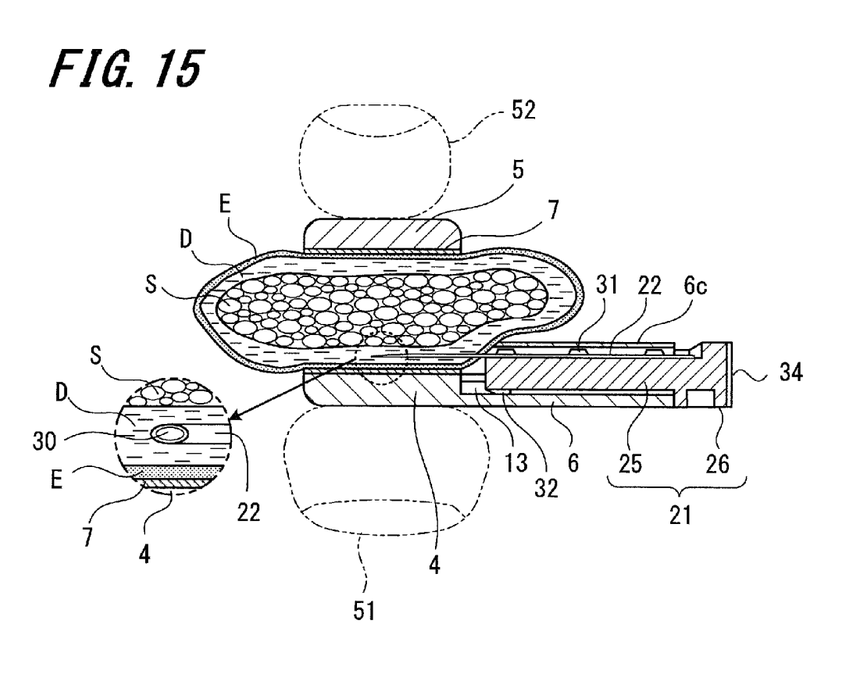
FIG. 15 is an explanatory diagram illustrating a state in FIG. 14 that the puncture needle has punctured the raised skin, in cross section in a lateral direction.

The puncture needle 22 is attached, as illustrated in FIG. 15 with the major part enlarged, such that the inclined surface of the needle tip where the drug solution outlet 30 is opened is substantially perpendicular to the surface of the first base plate 4 where the adhesive tape 7 has been attached. By attaching the puncture needle 22 to the slide member 21 in such a posture, even if the needle tip is bent by resistance from the skin at the time of puncturing, the bending direction of the needle tip can be made to coincide with the direction in which dermis extends. Accordingly, regardless of presence or non-presence of bending deformation of the needle tip of the puncture needle 22, it is possible to always cause the needle tip to coincide with dermis.

The drug solution injection port 24 is connected to the other end of the connection tube 23. To the drug solution injection port 24, for example, a syringe is detachably connected. The drug solution injection port 24 has a cylindrical port body, and the connection tube 23 is connected to one end thereof in the axial direction. And, to the other end of the port body, a flange part protruding outward in the radial direction is provided. As illustrated in FIG. 1, etc., a cap 44 is detachably mounted to the drug solution injection port 24. Note that in this example, the connection tube 23 is connected to the drug solution injection port 24, however, it may be configured such that without using the drug solution injection port 24, a syringe, a catheter connector, etc. is directly connected.

As the material of the slide member 21, for example, PP (polypropylene), PC (polycarbonate), and other hard plastics may be used. Note that the shape and the structure of the slide member 21 are not limited to those of the present example. For example, the guide part 14 mainly aims to prevent backlash between the guide member 6 and the slide member 21. Therefore, if the slide member 21 is the one in such a shape that backlash will not be present from the beginning, for example, a syringe-like one in a circular shape in cross section with a slide packing attached, it is possible to render the guide part 14 unnecessary.

However, as described above, when it is configured such that the drug solution outlet 30 of the puncture needle 22 always faces to a given direction by regulating the opening direction of the drug solution outlet 30, the guide part 14 is necessary. In this case also, it is needless to say that the shape and the structure of the guide part 14 are not limited to those in the above-described example.

A puncture needle moving device 10 movably supporting the puncture needle 22 is constituted by the guide member 6 and the slide member 21.

Figure 12:
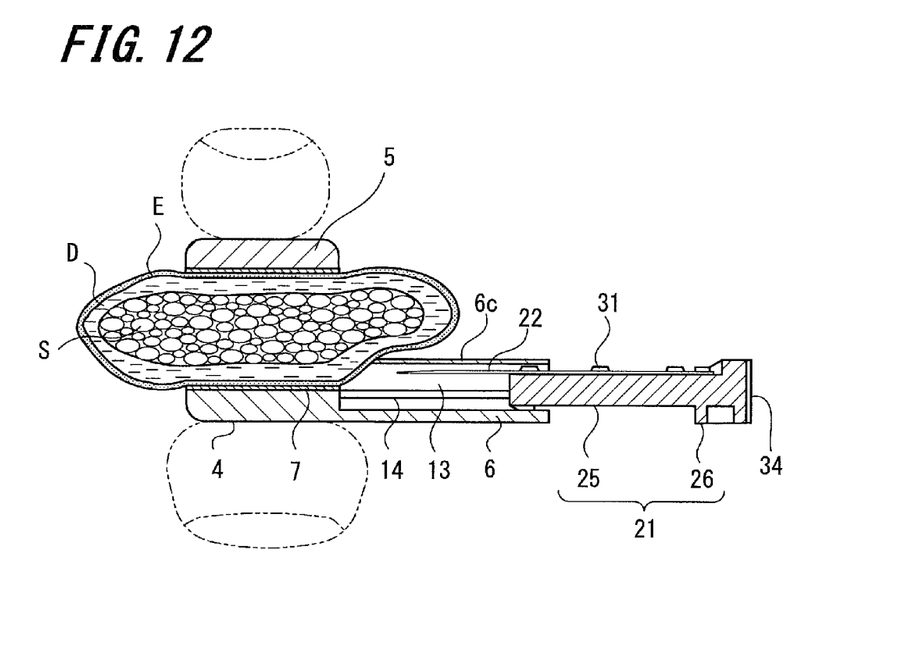
FIG. 12 is an explanatory diagram illustrating a state that the puncture device has been laterally sectioned together with the skin raised in FIG. 11.

The puncture device 1 is constituted by slidably mounting the moving unit 3 having such configuration to the fixing unit 2. FIG. 1 is a diagram illustrating an initial condition that the moving unit 3 illustrated in FIG. 3 has been installed to the fixing unit 2 illustrated in FIG. 2. At this time, as illustrated in FIG. 12, the needle tip of the puncture needle 22 is housed within the penetration hole 13 of the guide member 6. With such configuration, it is possible to protect the needle tip of the puncture needle 22 without providing a protection cover, etc. Therefore, when attaching the puncture device 1 to the body, it can be prevented that a finger, etc. touches the needle tip of the puncture needle 22 and that the puncture needle 22 is accidentally caused to puncture a finger, etc., so that the puncture needle 22 can be kept in a clean condition. Also, because it will never occur that the puncture needle 22 is directly subjected to stress from the outside, it is possible to prevent the puncture needle 22 from being deformed by stress.

The puncture device 1 having such structure can be used, for example, in the following manner. Generally, the puncture device 1 is packaged and sterilized and is distributed in a condition that the moving unit 3 has been assembled to the fixing unit 2, that is, a condition that the slide part 25 of the slide member 21 of the moving unit 3 has been fit in the penetration hole 13 of the guide member 6 of the fixing unit 2 (condition in FIG. 1). When the puncture device 1 is used, the puncture device 1 in the above-described assembled condition is taken out from the package, and is put in use.

Note that the puncture device 1 may be used in such a manner that it is not in an assembled condition in advance, and when using it, the moving unit 3 is assembled to the fixing unit 2. At this time, the needle tip of the puncture device 22 supported by the slide member 21 is placed within the penetration hole 13 so as not to protrude on the side of the adhesive tape 7 (see FIG. 12). Also, it will be no problem even if the moving unit 3 is installed to the fixing unit 2 after attaching the fixing unit 2 to skin.

Figure 9:
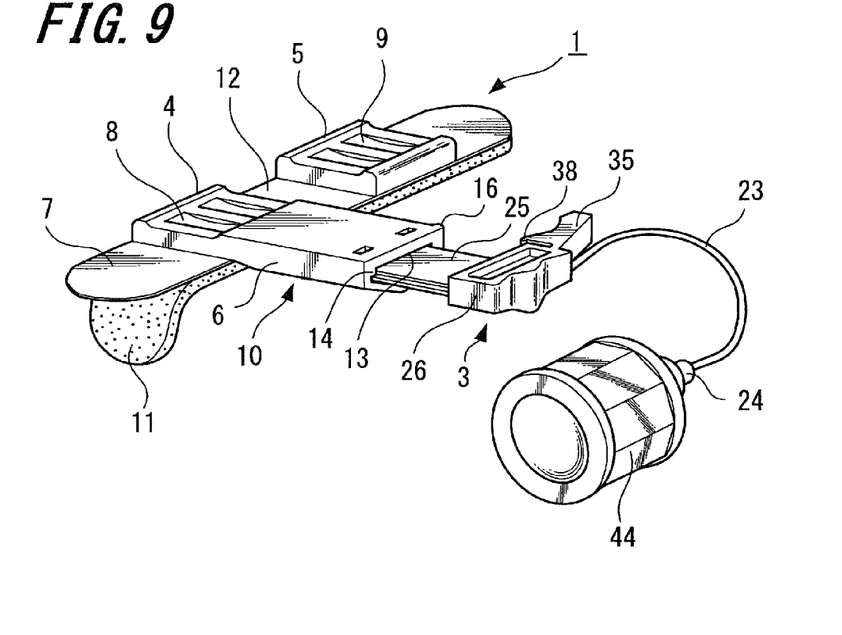
FIG. 9 is an explanatory diagram for explaining a usage form of the puncture device of the present invention, illustrating a state that a release paper is being peeled off.

Next, as illustrated in FIG. 9, the release paper 11 attached to the adhesive tape 7 of the fixing unit 2 is peeled off to expose the adhesive coated on the whole one surface of the adhesive tape 7. Then, the puncture device 1 is caused to adhere and is fixed to an appropriate place on a wrist, a forearm, an upper arm, or a leg portion, etc. That is, the surface of the adhesive tape 7 where the adhesive has been coated is pressed against a region of the skin of the user where the puncture device 1 is going to puncture, and the fixing unit 2 is caused to adhere to a given region of the skin through the adhesive tape 7. At this time, in the skin under the adhesive tape 7, epidermis E located most outside, dermis D located inside the epidermis E, and subcutaneous soft tissue S located inside the dermis D are arranged in layers (see FIG. 12 and FIG. 13).

Figure 10:
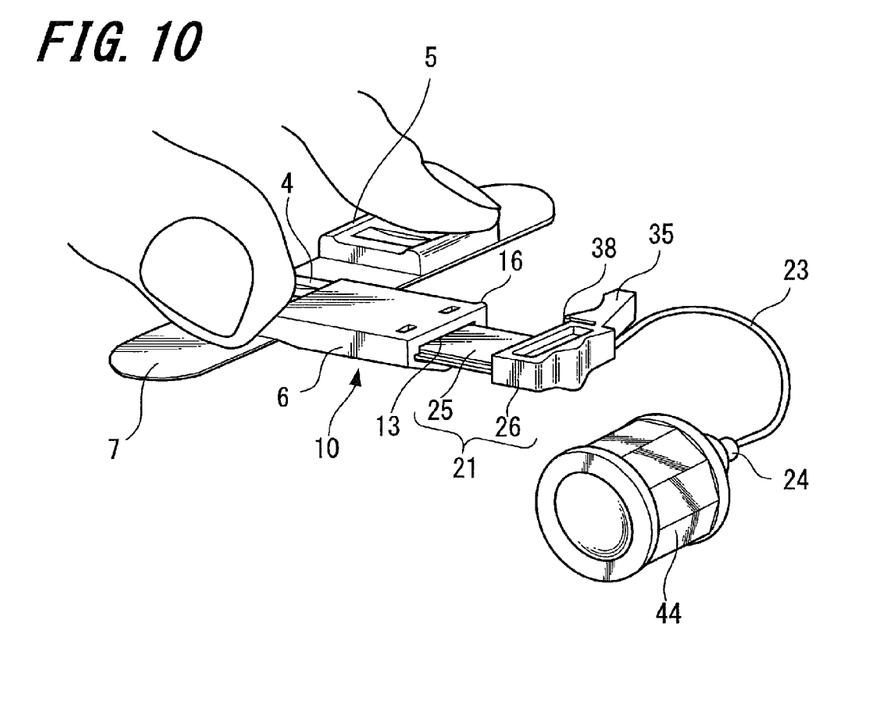
FIG. 10 is an explanatory diagram for explaining a usage form of the puncture device of the present invention, illustrating a state that two base plates are being pressed with a thumb and a forefinger.
Figure 11:
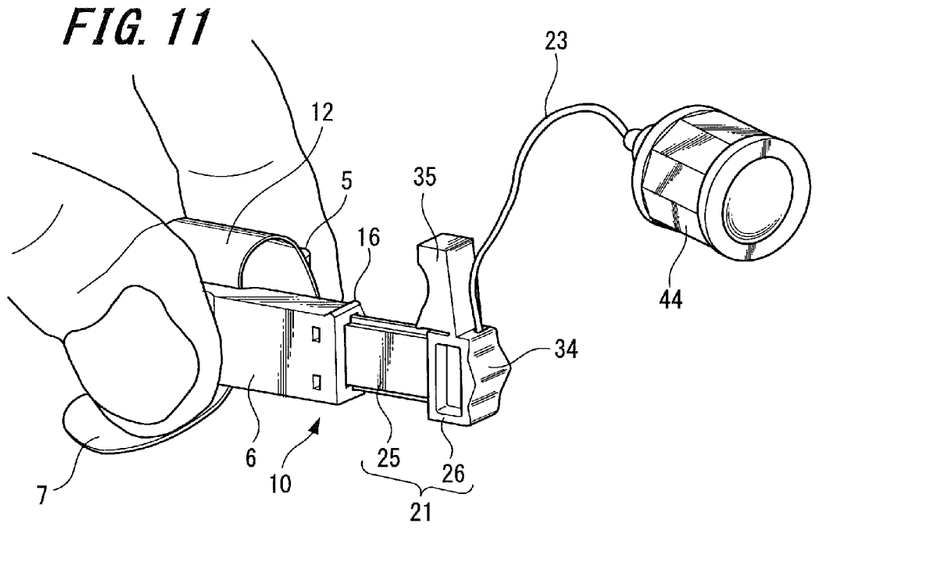
FIG. 11 is an explanatory diagram for explaining a usage form of the puncture device of the present invention, illustrating a state that the skin has been raised together with the two base plates with a thumb and a forefinger.

Next, as illustrated in FIG. 10, a thumb 51 of one hand is pressed against the anti-slip part 8 of the first base plate 4, and a forefinger 52 of the hand is pressed against the anti-slip part 9 of the second base plate 5. Then, as illustrated in FIG. 11, a portion of the skin is picked up together with the first base plate 4 and the second base plate 5 with the thumb 51 and the forefinger 52 of one hand. At this time, because the first base plate 4 and the second base plate 5 are connected to each other by means of the base connection part 12 having sufficiently large flexibility, it is possible to easily pick up a given portion of the skin, only as much as needed, with one hand. In addition, because the engagement convex part 32 for preventing falling off of the slide member 21 is engaged with the engagement reception part 15 of the guide member 6, there is no fear that the slide member 21 falls off the guide member 6 or the puncture needle 22 accidentally punctures skin.

Figure 13:
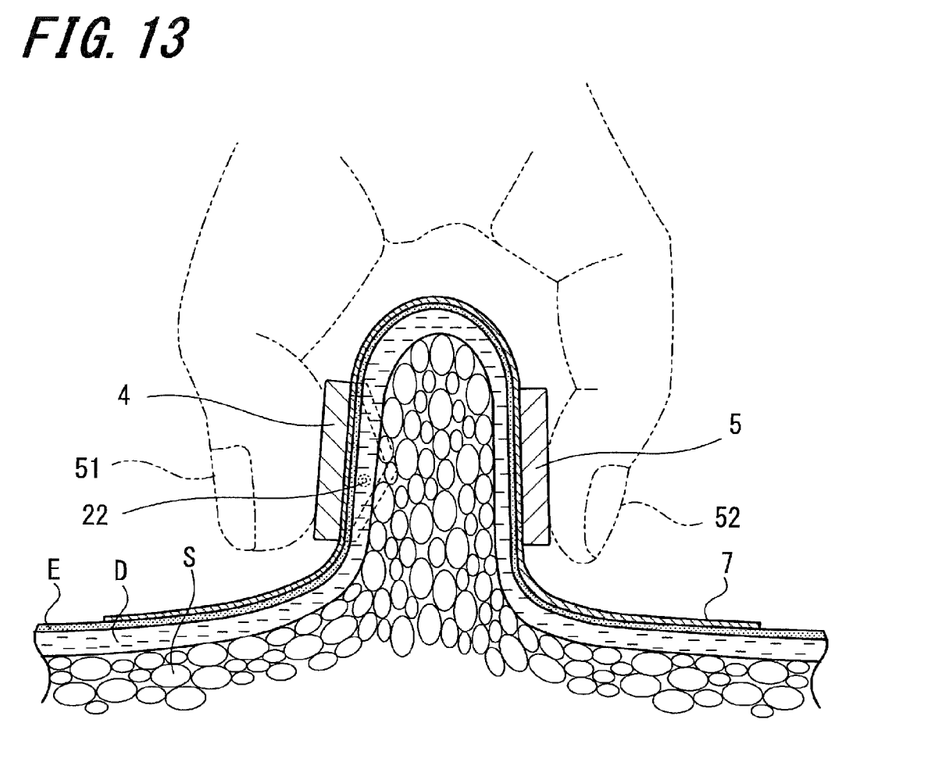
FIG. 13 is an explanatory diagram illustrating a state that the puncture device has been vertically sectioned together with the skin raised in FIG. 11.

Thereby, the picked-up portion of the skin is put in conditions illustrated in FIG. 12 and FIG. 13, and the first base plate 4 and the second base plate 5 face each other pinching the picked-up portion of the skin between them. At this time, a portion of the skin near the picked-up portion of the skin pinched between the first base plate 4 and the second base plate 5 is pressed by the inclined surfaces 6c, 6c, which are protruded portions of the guide member 6, and thereby a given step is formed in the skin. Due to the step in the skin formed at this time, it comes to a condition that the height (height from the reference plane of the first base plate 4) of the puncture needle 22 supported by the slide member 21 substantially coincides with the position of dermis D. The height from the skin surface (insertion depth) is achieved by setting the puncture needle storage part 29 in a predetermined position in advance. Note that the distance from the needle tip of the puncture needle 22 to the adhesive sheet 7 is preferably 0.2 mm or more and 5.0 mm or below.

Figure 14:
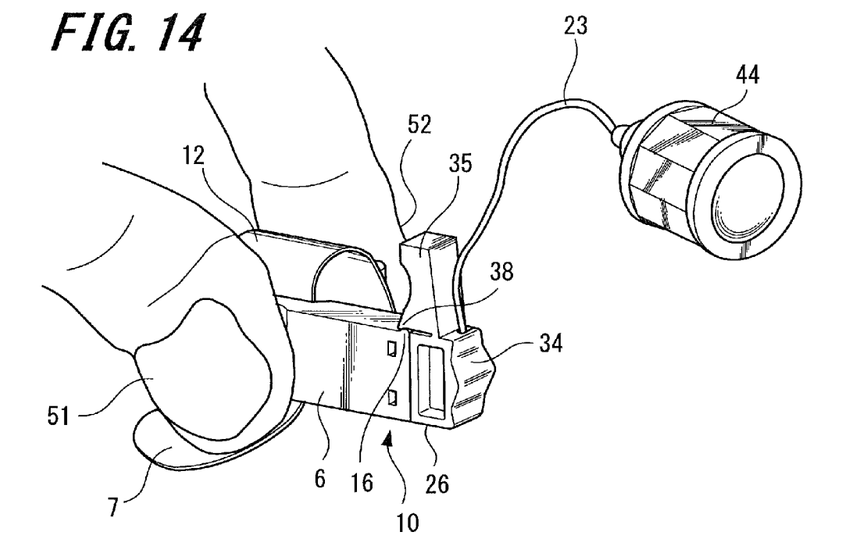
FIG. 14 is an explanatory diagram for explaining a usage form of the puncture device of the present invention, illustrating a state that after raising the skin together with the two base plates with a thumb and a forefinger, the puncture needle has punctured the raised skin.
Figure 16:
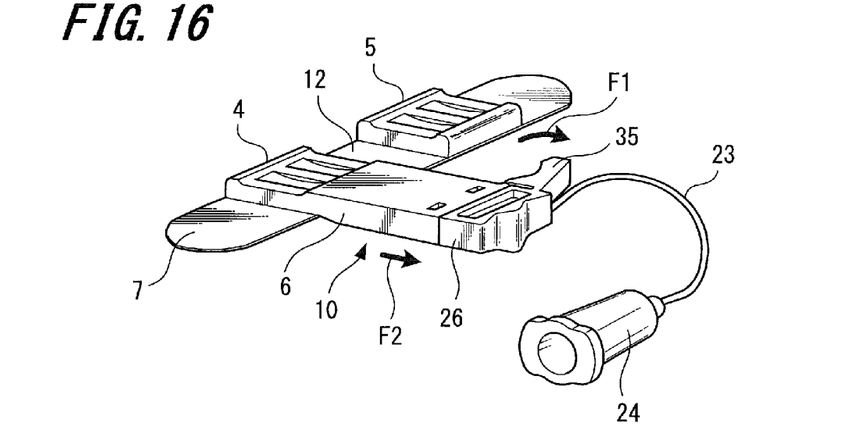
FIG. 16 is an explanatory diagram for explaining a usage form of the puncture device of the present invention, illustrating a state before pulling out a slide member from a guide member.
Figure 17:
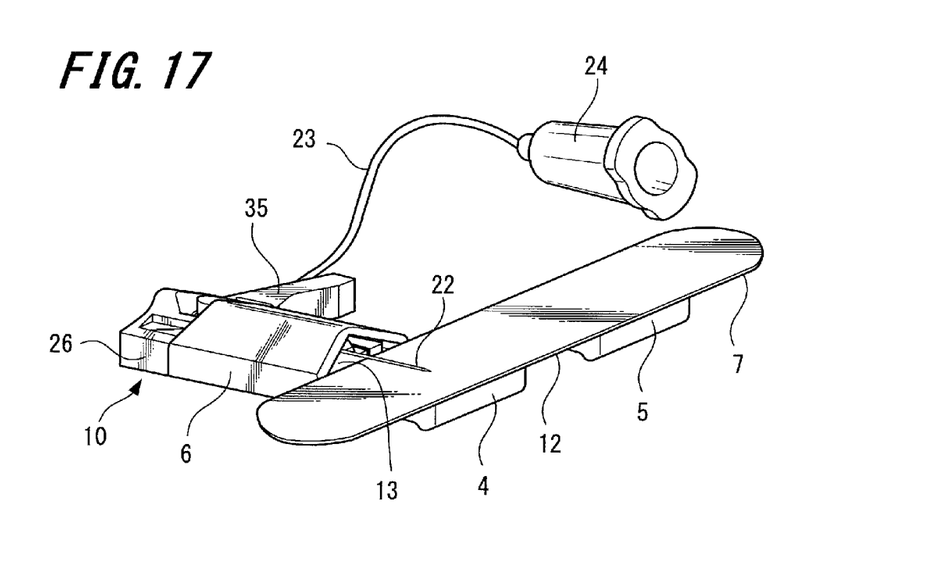
FIG. 17 is an explanatory diagram for explaining a usage form of the puncture device of the present invention, illustrating a state that a needle tip of a puncture needle has protruded from a penetration hole of the guide member.

Next, the slide member 21 is pushed in with the other hand, and as illustrated in FIG. 14 and FIG. 15, the puncture needle 22 supported by the slide part 25 is caused to be inserted in the skin. And, the slide member 21 is pushed until the head part 26 hits against the guide member 6. Thereby, the lock claw 38 provided in the lock lever 35 is brought into contact with the claw reception part 16 of the guide member 6, and thereafter, the lock claw 38 is rotated around the hinge part 37 by a reaction force from the claw reception part 16 and rides over the claw reception part 16. As a result, as illustrated in FIG. 16, the lock claw 38 is engaged with the claw reception part 16, and the slide member 21 is locked to the guide member 6. FIG. 17 is a diagram explaining a condition that the puncture needle 22 has protruded from the guide member 6.

As described above, the needle tip of the puncture needle 22 is formed to have an inclined surface cut in an inclined direction, and the drug solution outlet 30 is opened in the inclined surface. Therefore, when inserting the puncture needle 22 into skin, moment going in the direction perpendicular to the surface direction of the inclined surface acts on the puncture needle 22 because of resistance force from the skin. As a result, it follows that the puncture needle 22 bends in the direction perpendicular to the surface direction of the inclined surface, however, in this example, the puncture needle 22 is fixed to the slide member 21 with the surface direction of the inclined surface directed to the direction substantially perpendicular to the reference plane of the first base plate 4.

Thereby, it comes to that the puncture needle 22 bends in the direction parallel to the reference plane of the first base plate 4, however, dermis D is present extending in that direction. As a result, it is possible to cause the deformation direction of the needle tip to coincide with the direction in which dermis D extends, and it becomes possible to always keep the drug solution outlet 30 coincided with dermis D. Accordingly, it is possible to reliably insert the needle tip of the puncture needle 22 in the position of dermis D.

After insertion of the puncture needle 22, the thumb and the forefinger of one hand are released from the base plates 4, 5, and the puncture device 1 is returned to a free condition. Thereafter, the cap 44 attached to the drug solution injection port 24 is removed, and a syringe, etc. is connected to the drug solution injection port 24. Then, by operating the syringe, etc., a drug solution stored in the syringe, etc. is injected into the body. At this time, because there is no need to touch the puncture device 1, both hands can be used to operate the syringe, etc., and a quantitative operation can be easily carried out. Note that as the drug solution, given as medicine for injection, and various kinds of liquids containing macromolecular material, such as, hormone, antibody medicine, cytokine, vaccine, etc.

After the drug solution has been injected to the body, first, the puncture needle 22 is pulled out from skin by sliding the moving unit 3, and then, the fixing unit 2 is detached from the skin. The detaching operation of the slide member 21 is performed as follows. First, as illustrated in FIG. 16, a force F1 is applied to the lock lever 35 to rotate the lock lever 35 around the hinge part 37, and thereby locking of the lock claw 38 by the claw reception part 16 is released. Next, a force F2 is applied to the head part 26 to pull out the slide member 21 from the guide member 6. By this operation of pulling out the slide member 21, the puncture needle 22 fixed to the slide part 25 is pulled out at the same time from the skin.

Figure 18:
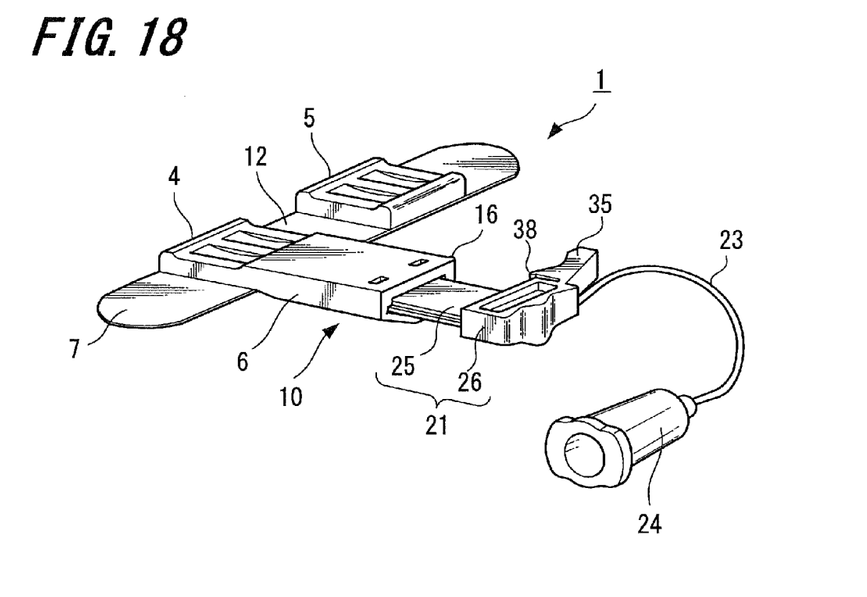
FIG. 18 is an explanatory diagram for explaining a usage form of the puncture device of the present invention, illustrating a state after the slide member has been pulled out from the guide member, viewed from one surface side.
Figure 19:
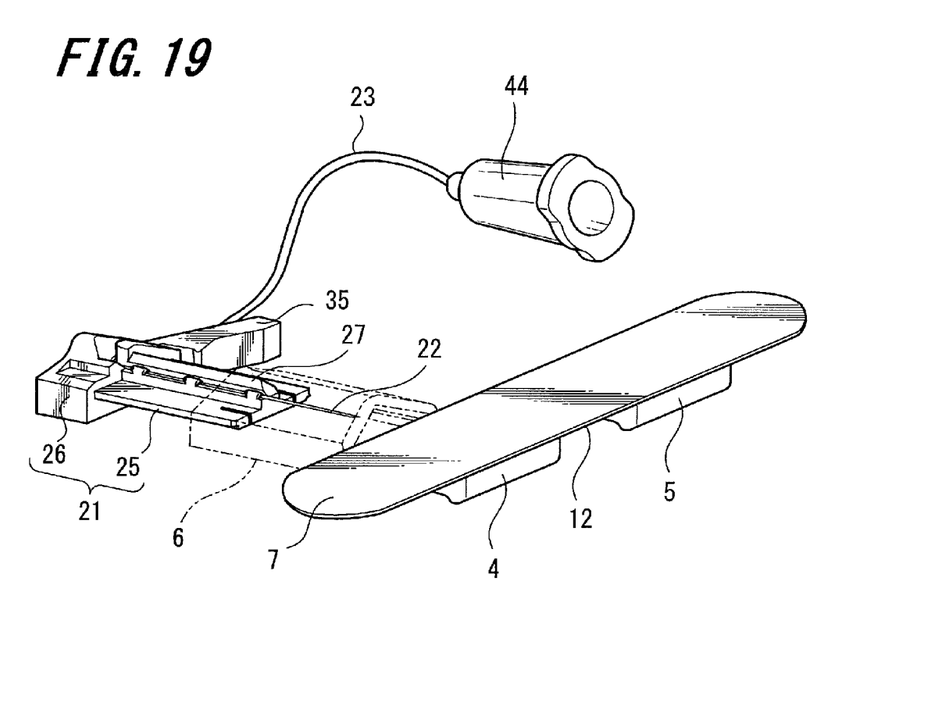
FIG. 19 is an explanatory diagram for explaining a usage form of the puncture device of the present invention, illustrating a state after the slide member has been pulled out from the guide member, viewed from the other surface side.

At this time, the engagement convex parts 32, 32 provided in the slide part 25 are engaged with the engagement reception parts 15, 15 provided in the guide member 6. By engagement of the engagement convex parts 32, 32 with the engagement reception parts 15, 15, as illustrated in FIG. 18, it is possible to surely prevent that the slide member 21 comes off the guide member 6. Note that by forming the front side in the insertion direction of the engagement convex part 32 in a tapered shape, the engagement convex part 32 can be easily separated relative to the engagement reception part 15 at the time of insertion. Further, after removing the puncture needle 22, the needle tip of the puncture needle 22 is held within the penetration hole 13 of the guide member 6 as illustrated in FIG. 19, so that it never occurs that the operator is injured by the puncture needle 22.

Thereafter, the adhesive tape 7 is detached from the skin, and the punctured device 1 is disposed as medical waste or subjected to recycling. At this time, by attaching the adhesive tape 7 to the guide member 6 and closing the penetration hole 13 with the adhesive tape 7, prevention of further erroneous puncturing is realized.

Note that in this example, a case has been described in which an injection needle is used as the puncture needle 22, however, the puncture needle 22 is not limited to the injection needle, and besides the injection needle, it is possible to use a needle with a sensor. For example, a catheter-type sensor, etc. may be given as an example, in which in a puncture needle, a catheter which covers the puncture needle is provided, and a detection unit for measuring components of body fluids is provided at a part of the catheter, and after puncturing the skin, the puncture needle is removed and the catheter is indwelled. Such indwelling-type sensors include a micro-dialysis sensor, a fluorescence sensor containing a fluorescent dye of phenyl boronic acid type for measuring sugar, an electrode sensor in which enzyme has been fixed, etc.

Also, in the embodiment of the present invention, for the means for causing the fixing unit to adhere to the skin, an adhesive tape has been used, however, the adhesive means is not limited to the adhesive tape. For example, those having such structure that the skin is hard to slide may be used, for example, a resin material having a high friction coefficient relative to skin, a sheet member having a plurality of minute protrusions on the surface thereof, etc.

According to the puncture device 1 of the present embodiment, it is possible to cause the puncture needle 22 to puncture skin and the needle tip to reliably reach dermis D as a given region, in a condition that the puncture device 1 is surely fixed to the body. Thereby, it is possible to reliably inject a drug solution, etc. to a given region, such as dermis, etc. Note that the injection region of a drug solution, etc. is not limited to dermis D, and for example, it may be configured such that a drug solution, etc. is injected to subcutaneous soft tissue S under the dermis D.

The puncture device of the present invention is not limited to the embodiment described above, and it is needless to say that various variations and modifications are possible in configuration, shape, material, etc. within the scope not departing from the configuration of the present invention.

Note that the puncture device of the above-described embodiment may be configured so as to be used just one time in a disposable manner, or reused two times or more by carrying out a sterilization treatment after use.

The invention claimed is:

1. A puncture device comprising:
   a first base plate;
   a second base plate;
   a base plate connection part having flexibility and connecting the first base plate and the second base plate in a horizontal direction;
   an adhesive means provided to surfaces in a same direction of the first base plate and the second base plate; and
   a puncture needle moving means provided in the first base plate and movably supporting a puncture needle,
   wherein the first base plate and the second base plate are configured to rotate around a center portion of the base plate connection part to face each other and pinch skin adhered to the adhesive means,
   wherein the puncture needle is supported away from a surface of the adhesive means by a given distance and movable substantially in parallel to the surface of the adhesive means, and
   wherein when skin to which the adhesive means had adhered has been picked up by being pinched by the first base plate and the second base plate, the puncture needle is moved by the puncture needle moving means to puncture the picked up skin in parallel with an axis of rotation of the first base plate and the second base plate.

2. The puncture device according to claim 1, wherein the puncture needle moving means includes a slide member supporting the puncture needle, and a guide member supporting the slide member in a linearly-movable manner.

3. The puncture device according to claim 2, wherein the puncture needle moving means includes a locking means capable of locking the slide member at a given position of the guide member and releasing such locking.

4. The puncture device according to claim 2, wherein the guide member includes a cylindrical body having a penetration hole opened at both ends thereof, and a guide part preventing rotation and enabling only linear movement of the slide member is provided in the penetration hole.

5. The puncture device according to claim 1, wherein the first base plate, the second base plate, and the base plate connection part are integrally formed by synthetic resin.

6. The puncture device according to claim 2, wherein in the puncture needle, a blade edge is formed at a tip, and wherein the slide member supports the puncture needle with an inclined surface of the blade edge directed in a direction substantially orthogonal to the surface of the adhesive means.

7. The puncture device according to claim 2, wherein one end of a drug solution injection port is connected to a base end of the puncture needle, within the slide member.

8. A puncture device for puncturing human skin comprising:
   a flexible base plate connection part having an upper surface, a lower surface, a center portion and an axis passing through the center portion;
   a first base plate having a lower surface fixed to the upper surface of the base plate connection part;
   a second base plate having a lower surface fixed to the upper surface of the base plate connection part, the center portion of the base plate connection part extending between the first base plate and the second base plate;
   an adhesive layer applied to the lower surface of the base plate connection part for adhering to the human skin;
   a puncture needle spaced apart from the adhesive layer and movable in a direction parallel to the adhesive layer so that the puncture needle does not contact the adhesive layer;
   a puncture needle moving member movably mounted on the first base plate and supporting the puncture needle;
   wherein the flexible base plate connection part folds around the axis passing through the center portion so that the lower surface of the first base plate faces the lower surface of the second base plate while the human skin adhered to the adhesive layer is pinched between the first base plate and the second base plate; and
   wherein the puncture needle moving member guides movement of the puncture needle so that the puncture needle moves in a direction parallel to the axis passing through the center portion and so that the puncture needle punctures the human skin pinched between the first base plate and the second base plate.

9. The puncture device of claim 8, wherein the puncture needle moving member comprises a hollow guide member fixed to the first base plate and a slide member slidably connected to and movable through the hollow guide member, the puncture needle being fixed to the slide member and extending away from the slide member.

10. The puncture device of claim 9, wherein the hollow guide member encloses a portion of the slide member and a portion of the puncture needle as the slide member and puncture needle move together through the hollow guide member so that the puncture needle moves in the direction parallel to the center axis.

11. The puncture device of claim 9, further comprising a protrusion extending away from the slide member, the protrusion and the puncture needle being positioned at opposing ends of the slide member, the protrusion allowing a user to push the slide member and the puncture needle together through the hollow guide member.

12. The puncture device of claim 8, the flexible base plate connection part, the first base plate and the second base plate being integrally formed of a synthetic resin.

13. A puncture device for puncturing human skin comprising:
   a first base plate;
   a second base plate;
   a flexible connection part connecting together the first base plate and the second base plate, the flexible connection part possessing a center portion located between the first and second base plates;
   adhesive underlying both the first base plate and the second base plate and having a surface to adhere to the human skin;
   a puncture needle possessing an axis;
   a slide member slidably mounted on the first base plate so that the slide member is slidably movable relative to the first base plate, the puncture needle being fixed to the slide member to slide together with the slide member;
   the first and second base plates being movable towards one another when the adhesive is adhered to the human skin to fold the flexible connection part at the center portion of the flexible connection part while pinching a portion of the human skin between the first and second base plates; and
   the slide member positioning the puncture needle and guiding the sliding movement of the puncture needle so that the puncture needle slidably moves along the axis of the puncture needle from a position, before pinching the human skin, in which the axis of the puncture needle is spaced from and positioned below the surface of the adhesive when the puncture device is oriented so that the surface of the adhesive is downwardly facing, to a position after pinching the human skin in which the puncture needle punctures the pinched human skin.

14. The puncture device according to claim 13, wherein the wherein flexible connection part is a part of an adhesive tape having one surface on which is located the adhesive, and an other surface opposite the one surface.

15. The puncture device according to claim 13, wherein the first and second base plates are secured to the other surface of the adhesive tape.

16. The puncture device according to claim 13, further comprising an injection port connected to an interior of the puncture needle by connection tubing to introduce solution into the puncture needle.

* * * * *